(12) United States Patent
Boss et al.

(10) Patent No.: US 6,406,777 B1
(45) Date of Patent: Jun. 18, 2002

(54) METAL AND GLASS STRUCTURE FOR USE IN SURFACE ENHANCED RAMAN SPECTROSCOPY AND METHOD FOR FABRICATING SAME

(75) Inventors: Pamela A. Boss; Roger D. Boss, both of San Diego; Stephen H. Lieberman, La Mesa, all of CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 63 days.

(21) Appl. No.: 09/593,675

(22) Filed: Jun. 14, 2000

(51) Int. Cl.⁷ .................. B32B 15/00; B32B 15/20; B32B 3/00
(52) U.S. Cl. .................. 428/209; 428/201; 428/203; 428/210; 428/426; 428/672; 428/673; 428/674
(58) Field of Search .................. 428/201, 203, 428/209, 210, 426, 672, 673, 674

(56) References Cited

U.S. PATENT DOCUMENTS

| | | |
|---|---|---|
| 4,888,204 A | 12/1989 | Tutt et al. |
| 5,395,650 A | 3/1995 | Holl et al. |
| 5,424,133 A | 6/1995 | Eckhardt et al. |
| 5,472,881 A | 12/1995 | Beebe et al. |
| 5,514,501 A | 5/1996 | Tarlov |
| 5,527,712 A * | 6/1996 | Sheehy .................. 436/525 |
| 5,693,152 A | 12/1997 | Carron |
| 5,716,705 A | 2/1998 | Wirth et al. |
| 5,827,417 A | 10/1998 | Porter et al. |
| 5,837,552 A | 11/1998 | Cotton et al. |

OTHER PUBLICATIONS

Mosier–Boss et al., "Comparison of Three Methods to Improve Adherence of Thin Gold Films to Glass Substrates and Their Effect on the SERS Response", *Applied Spectroscopy*, vol. 53, No. 7, 1999, pp. 862–873 (No month).

* cited by examiner

Primary Examiner—Deborah Jones
Assistant Examiner—Andrew T Piziali
(74) Attorney, Agent, or Firm—Harvey Fendelman; Michael A. Kagan; Peter A. Lipovsky

(57) ABSTRACT

A surface enhanced Raman scattering structure may be used for detecting analytes such as organic contaminants in air and aqueous environments, and metallic and anionic contaminants in water. The structure is fabricated by etching a surface of a glass substrate to form a roughened surface; creating an adhesion layer on the roughened surface; forming metal islands, such as gold, silver, or copper, on the adhesion layer to create a composite structure; and placing the composite structure in a thiol solution to form a self-assembled monolayer over the metal islands. The thiol solution is selected to attract an analyte of interest. The roughened surface enhances the SERS response of the structure and preferably has an average surface roughness that does not exceed about 2500 Å and a periodicity that does not exceed about 12.5 microns.

7 Claims, 9 Drawing Sheets

METAL AND GLASS STRUCTURE FOR USE IN SURFACE ENHANCED RAMAN SPECTROSCOPY AND METHOD FOR FABRICATING SAME

BACKGROUND OF THE INVENTION

The present invention generally relates to the field of surface enhanced Raman spectroscopy, and more particularly, to a method for bonding metallic films to a glass substrate to create a structure suitable for use in surface enhanced Raman spectroscopy.

In the 1970s, it was discovered that Raman scattering from molecules of an analyte of interest adsorbed on noble metals such as silver, copper, and gold when irradiated with optical energy can be enhanced by as much as $10^6$ to $10^7$ compared to merely irradiating the analyte. This phenomenon is known as surface enhanced Raman spectroscopy (SERS). A SERS structure generally includes a metal layer formed on a substrate and is used to detect the presence of an analyte by examining the emissions from the substrate when irradiated with optical energy. SERS emissions, or spectra, have been used to detect and identify trace organics and as a detection method in gas chromatography, liquid chromatography, and thin layer chromatography. Electrochemical SERS and SERS of chemically modified surfaces have been used to detect aromatic compounds and chlorinated hydrocarbons and other organic contaminants of environmental concern in the ppm range.

The generation of SERS spectra for molecules adsorbed on metal surfaces requires that the metal surface be roughened. The most common types of SERS substrates include electrodes, colloidal solutions, island films prepared by vacuum deposition of metal and metal-covered surfaces having submicrometer structures such as micro spheres, monolithic posts, etc.

The SERS phenomenon is wavelength dependent. In general, greater enhancements are observed using near infrared (IR) excitation. However, water strongly absorbs near IR energy. Consequently, the SERS emissions obtained for aqueous samples tend to be greatly attenuated. The more water through which the excitation energy must penetrate, the greater is the attenuation. Therefore, there is a strong motivation to develop a SERS system for detecting analytes of interest in an aqueous environment that minimizes attenuation of the IR excitation signal.

The use of SERS techniques in an aqueous environment strongly suggests the need for a method for fabricating a thin, transparent, and durable metal layer on an optically transparent substrate, such as glass, to create a composite transparent structure. A transparent substrate would be desirable so that the interface at the aqueous environment adjacent to the transparent composite structure could be illuminated with minimal attenuation of excitation energy through water. If an analyte of interest is present, SERS spectra will be emitted from the surface of the composite transparent structure at the interface and directed back through the structure to an optical receiver.

One type of composite transparent structure suitable for use in SERS includes silver films that are vapor deposited onto an optically transparent substrate made of silicon oxide ($SiO_2$), such as glass. However, metals such as gold and silver do not adhere well to glass. Significant exposure to water damages the metal films, thereby limiting their applicability in aqueous environments. Therefore, a need exists for a method for securely forming metal films onto a transparent substrate that produces a durable structure suitable for generating SERS spectra. A further need exits for manufacturing a SERS structure that is durable in aqueous environments.

SUMMARY OF THE INVENTION

The present invention provides a SERS structure for detecting an analyte of interest that exhibits high SERS activity and good adhesion to glass. Such substrates may be used in aqueous environments for extended periods of time. The SERS substrate includes a glass substrate having a specially roughened surface on which an adhesion layer is formed. A discontinuous noble metal layer is formed, as for example, by vapor deposition on the adhesion layer. A thiol coating covers and protects the metal layer from chemical contamination, thereby extending the lifetime of the structure to months when exposed to an aqueous environment. The type of thiol of which the coating consists is selected to have an affinity for the analyte. The roughened surface provides the structure with a good SERS response.

A SERS structure may also be manufactured by subjecting a smooth surface of a transparent glass substrate to a silanization agent to create an adhesion layer, and then forming a metal layer on the adhesion layer. Next, the metal layer is subjected to an electrochemical etch which transforms the metal layer into electrically isolated metal islands. Finally, the metal islands are subjected to a thiol solution which forms a self-assembled monolayer that protects the islands and provides the SERS structure with sensitivity for particular agents of interest. The metal layer preferably consists essentially of a metal selected from the group that includes copper, gold, and silver. In the preferred embodiment, the silanization agent is a 1:10 mixture by volume of (3-mercaptopropyl) trimethoxysilane in ethanol.

The metal layer of the SERS substrate embodied in the present invention is very durable compared to those of prior art structures. Therefore, the present invention should find wide application in the application of SERS techniques for detecting organic contaminants in air and aqueous environments, and for detecting metallic and anionic contaminants in water.

These and other advantages of the invention will become more apparent upon review of the accompanying drawings and specification, including the claims.

BRIEF DESCRIPTION OF THE DRAWINGS

Throughout the several views, like elements are referenced using like references.

DESCRIPTION OF THE PREFERRED EMBODIMENT

Figure 1:
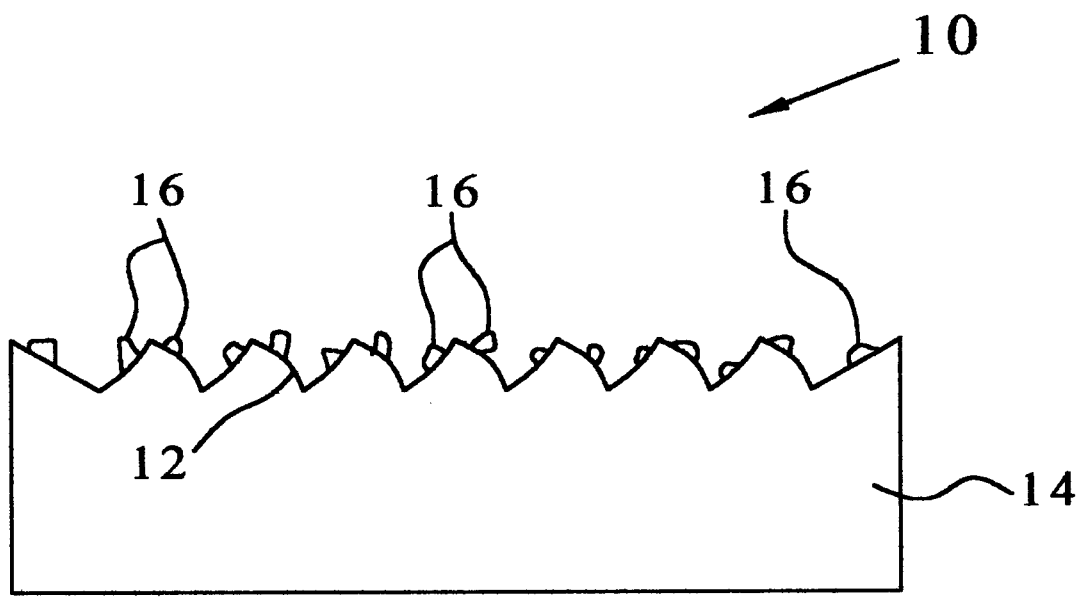
FIG. 1A is a cross-sectional view of a SERS structure embodying various features of the present invention.
FIG. 1B is an enlarged view of a section of the structure depicted in FIG. 1A.
Figure 1:
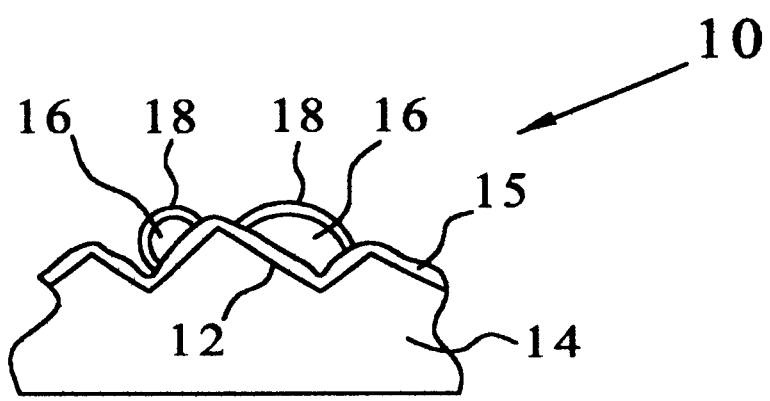

The present invention is directed to a surface enhanced Raman scattering (SERS) structure that includes metal islands formed on the roughened surface of transparent substrate such as transparent glass. When in contact with an analyte of interest and illuminated with appropriate excitation energy, a SERS structure will produce spectra having unique characteristics that are used to detect the analyte. By way of example, analytes may include organic, metallic, and anionic contaminants. Referring to FIGS. 1A and 1B, SERS structure 10 includes a specially roughened surface 12 of a glass substrate 14 on which an adhesion layer 15 is formed. Adhesion layer 15 promotes the bonding of the metal islands 16 to the glass substrate 14. The metal islands 16 are formed, as for example, by vapor deposition, on adhesion layer 15 to create a metal patterned substrate 11, shown in FIG. 4. A thiol coating, or self-assembled monolayer 18 on metal islands 16 protects metal islands 16 from chemical contamination, thereby extending the lifetime of structure 10 when exposed to aqueous environments from minutes or hours to months. The roughened surface 12 facilitates both a good SERS response and adhesion of the metal islands 16 to the substrate 14.

In the fabrication of structure 10, transparent substrate 14, such as a clear borosilicate glass slide, is carefully cleaned and prepared prior to having a metal film deposited on it. First, substrate 14 is immersed in a heated or boiling liquid reagent or reagents to remove any oils, metallic materials, and other contaminants that may be present on substrate 14. By way of example, a clear glass substrate 14 may be immersed in a Pyrex beaker containing boiling nitric acid for about 30 minutes. However, other liquid reagents also may be used such as hydrofluoric acid, hydrochloric acid, potassium hydroxide. Next, substrate 14 is removed from the boiling nitric acid and rinsed in either deionized or distilled water. After the water rinse, substrate 14 is immersed in hot or boiling methanol for about 30 minutes, followed by immersion in boiling acetone for about 30 minutes. This procedure removes any remaining organic contaminants. Substrate 14 is then removed from the methanol and allowed to air dry, as for example, about 1 hour.

Figure 2:
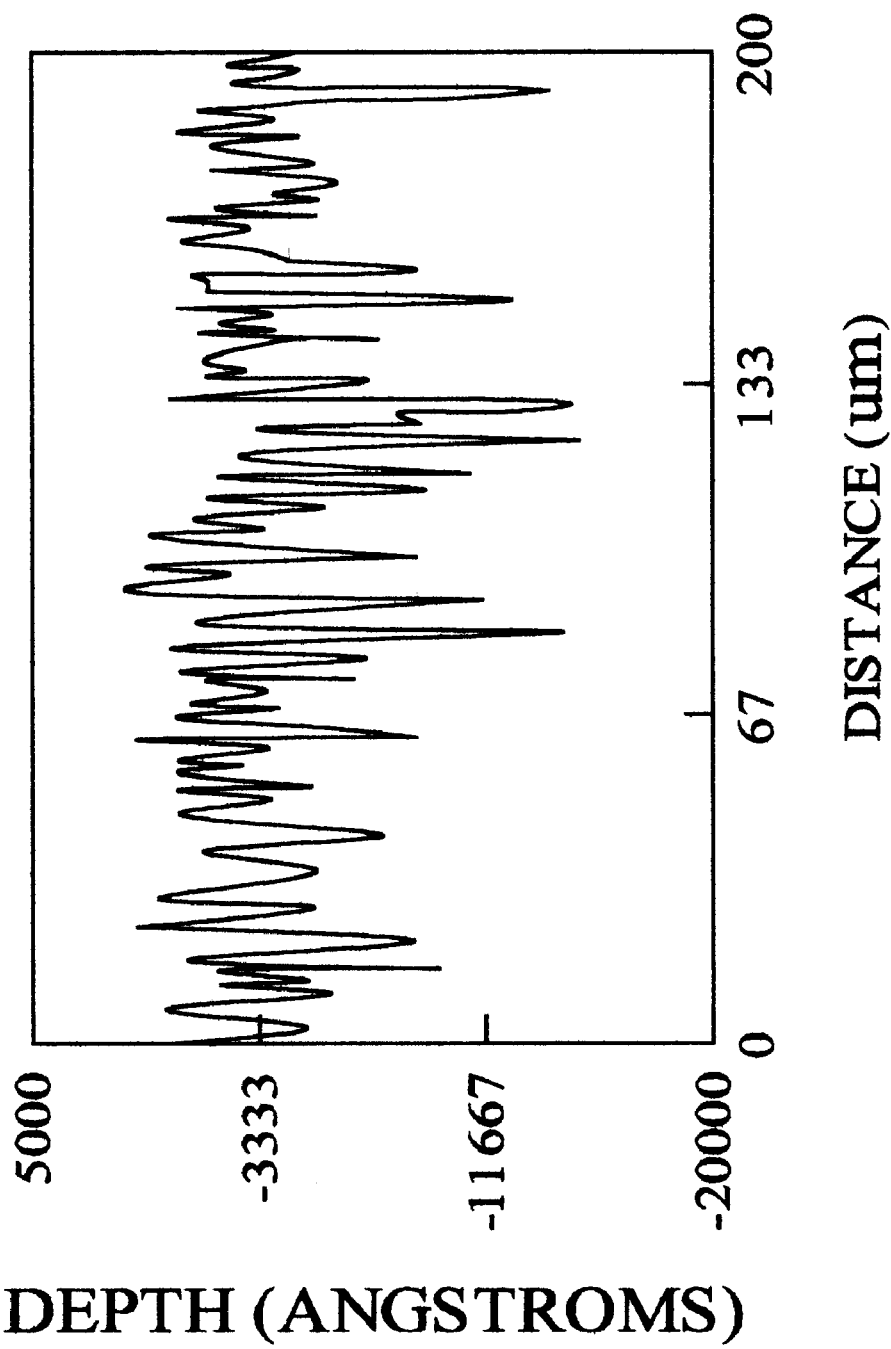
FIG. 2 is a surface profile of the roughened surface of the substrate used in the SERS structure of FIG. 1A.

Referring to FIG. 2, cleaned surface 12 of substrate 14 is etched to provide surface 12 with a surface roughness having a maximum peak to valley depth of about 16,000 Å, an average peak to valley depth of about 2,500 Å, and a peak to peak periodicity of about 12.5 microns. The roughness of surface 12 and its periodicity was measured using a Dektak³ST Surface Profiler (Vecco Sloan Technology). In contrast, commercial white glass generally has a surface having a peak to valley depth of about 200,000 Å, an average peak to valley depth of about 43,700 Å, and a peak to peak periodicity of about 100 microns. The combination of surface roughness and peak to peak periodicity of surface 12 provides structure 10 with a greatly enhanced SERS response compared to that of SERS structures that include commercial glass. In one implementation of the invention, surface 12 may be etched using a chemical etchant such as an HF based cream such as Velvet Etching Cream, manufactured by McKay International. Experience has shown that etching the glass for approximately 1 minute provides the surface roughness characteristics described above. Alternatively, surface 12 may be roughened using standard photolithographic techniques.

Figure 3:
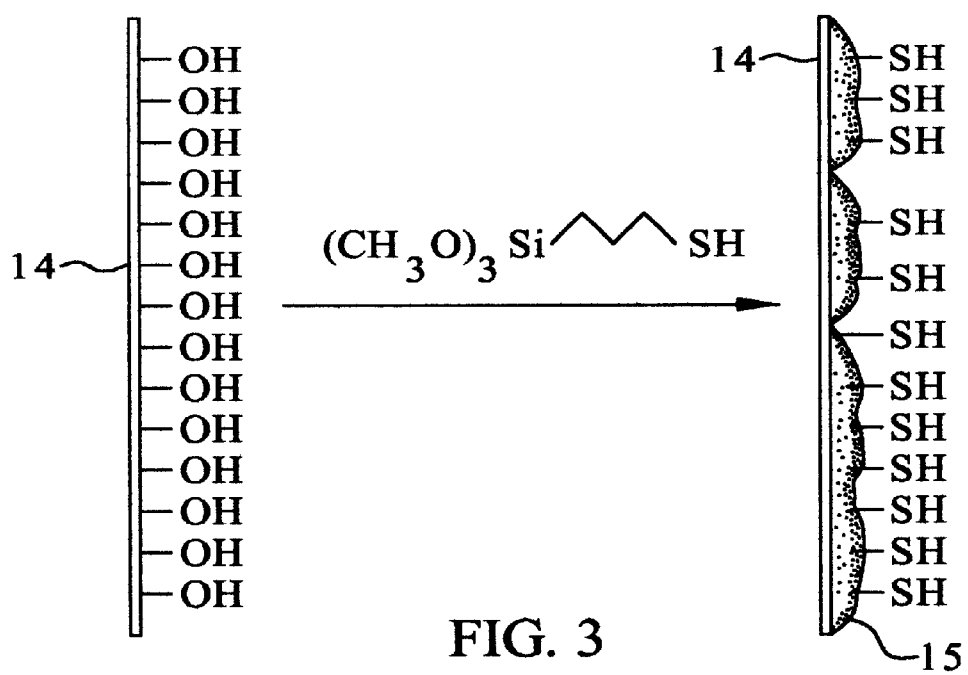
FIG. 3 represents the formation of a silane layer on surface of a glass substrate in the manufacture of the invention.

After etching, structure 14 is rinsed with distilled or deionized water, followed by an ethanol rinse. The cleaned, etched substrate 14 is then derivitized in a silanization agent such as a 1:10 mixture by volume of (3-mercaptopropyl) trimethoxysilane (MCTMS) in ethanol for about 24 hours to form adhesion layer 15 on roughened surface 12. As shown in FIG. 3, it is believed that the derivitization process causes a silane layer to bond to $^-$OH functional groups believed to be present on surface 12 when substrate 14 is implemented as a transparent glass substrate. Substrate 14 was next rinsed in ethanol to remove unreacted (3-mercaptopropyl) trimethoxysilane and allowed to air dry. Adhesion layer 15 promotes bonding between roughened surface 12 and metal islands 16.

Figure 8:
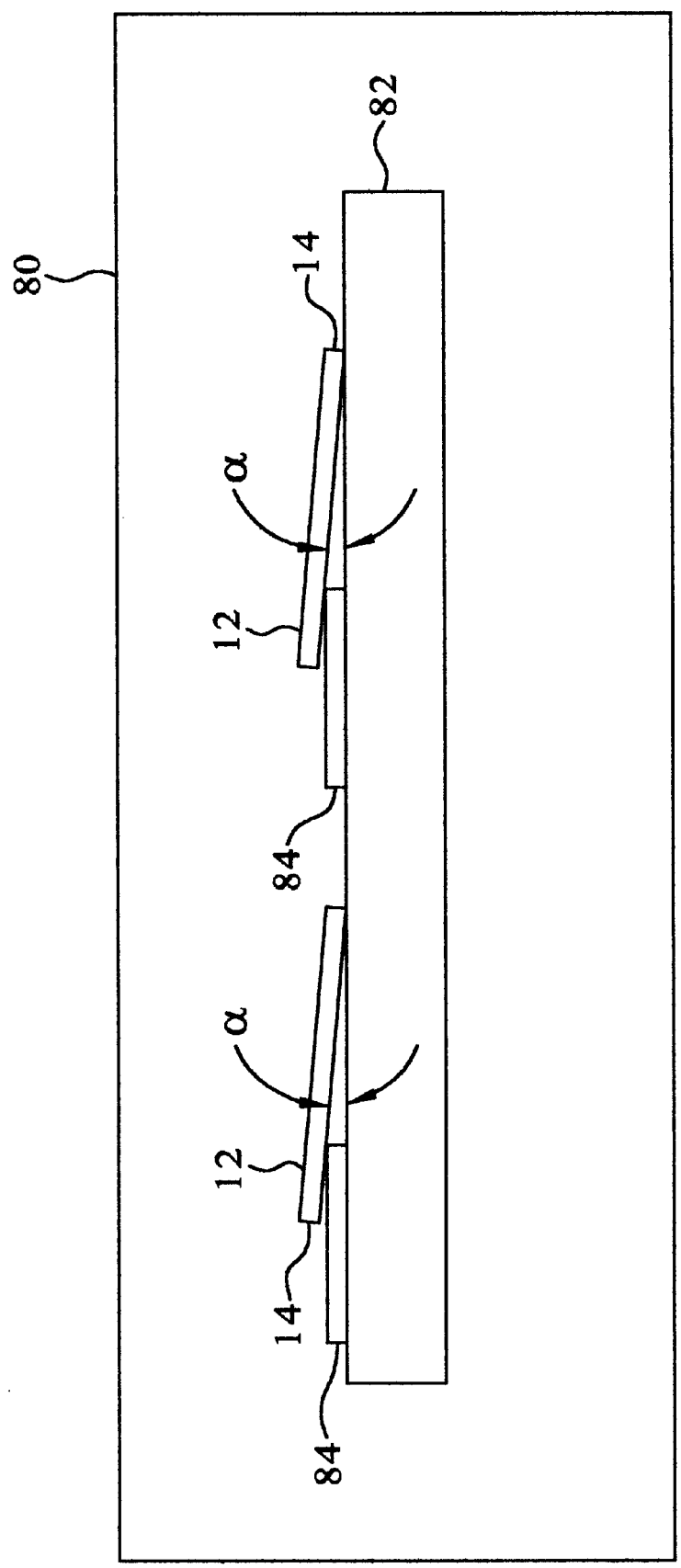
FIG. 8 shows glass substrates mounted at an angle in a vapor deposition system in the manufacture of the present invention.

When metal islands 16 are formed by vapor deposition, as shown in FIG. 8, one or more cleaned substrates 14 are positioned so that they each rest on both a stainless steel spacer 84 and on support structure 82 in a vapor deposition system 80 so that roughened surfaces 12 face upwardly at a slight angle α with respect to the horizontal. The angle may be in the range, for example, of about 3–5°, and more preferably, 4.5°. The purpose of canting substrate 14 at an angle with respect to the horizontal is to create "shadows" that prevent the deposited metal that comprises metal islands 16 from forming a continuous metal layer on roughened surface 12. In other words, it is desirable for metal islands 16 to have discontinuities that have been shown to enhance the SERS response of structure 10. By way of example, a metal such as gold, silver, or copper may be vapor deposited onto adhesion layer 15 to form metal islands 16. In one implementation of the invention, gold islands were vapor deposited onto roughened surface 12 using material evaporated from an Aldrich, 99.99% pure gold wire. Vapor deposition system 80 may be implemented as a Vecco Model EC 200 vapor deposition system. As a result of the aforesaid processing, adhesion layer 15 durably bonds metal islands 16 to roughended surface 12 so that structure 10 may provide an effective SERS response after being immersed in an aqueous environment for months.

Figure 4:
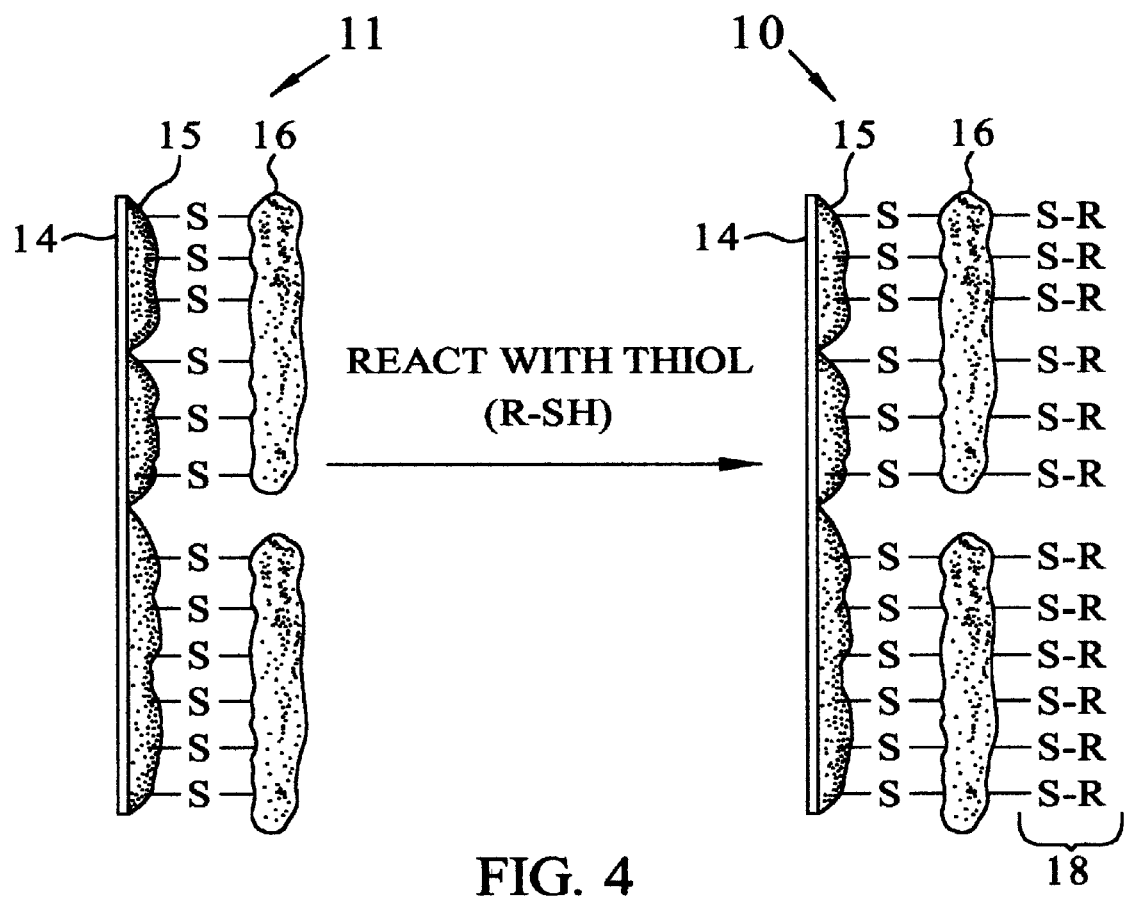
FIG. 4 shows the formation of a self-assembled monolayer (SAM) layer on the metal islands bonded to the glass substrate in the manufacture of the SERS structure of FIG. 1.

After depositing metal islands 16 onto adhesion layer 15 a patterned metal structure 11, as shown in FIG. 4, is created. Patterned metal structure 11 may be placed in a dilute ethanolic thiol solution at ambient temperature and pressure for a period of time, such as 24 hours. While structure 11 is soaking in the thiol solution, metal islands 16 react with the thiol to form a durable, self-assembled monolayer 18 on the metal islands 16, as shown in FIG. 4. Thiol coatings may be selected which have an affinity for the analyte (organic compounds, metal ions, or anions) of interest. Moreover, detection limits in the ppb to ppm range are possible. TABLE 1 provides, by way of example, a list of examples of thiols and analytes that may be detected using such thiol coatings. However, TABLE 1 is not to be considered exhaustive.

TABLE 1

| Thiol Type: | Usefull For Detecting: |
| --- | --- |
| 1-propanethiol | Benzene, toluene, ethylbenzene, xylene) and chlorinated solvents |
| cysteamine hydrochloride | anions such as nitrate and sulfate |
| 4-(2-pyridylazo) resorcinol modified with a disulfide group | Pb++, Cd++, and Cu++ |
| thiol derivatized dibenzo 18-crown-6 | alkali metals |

Figure 5:
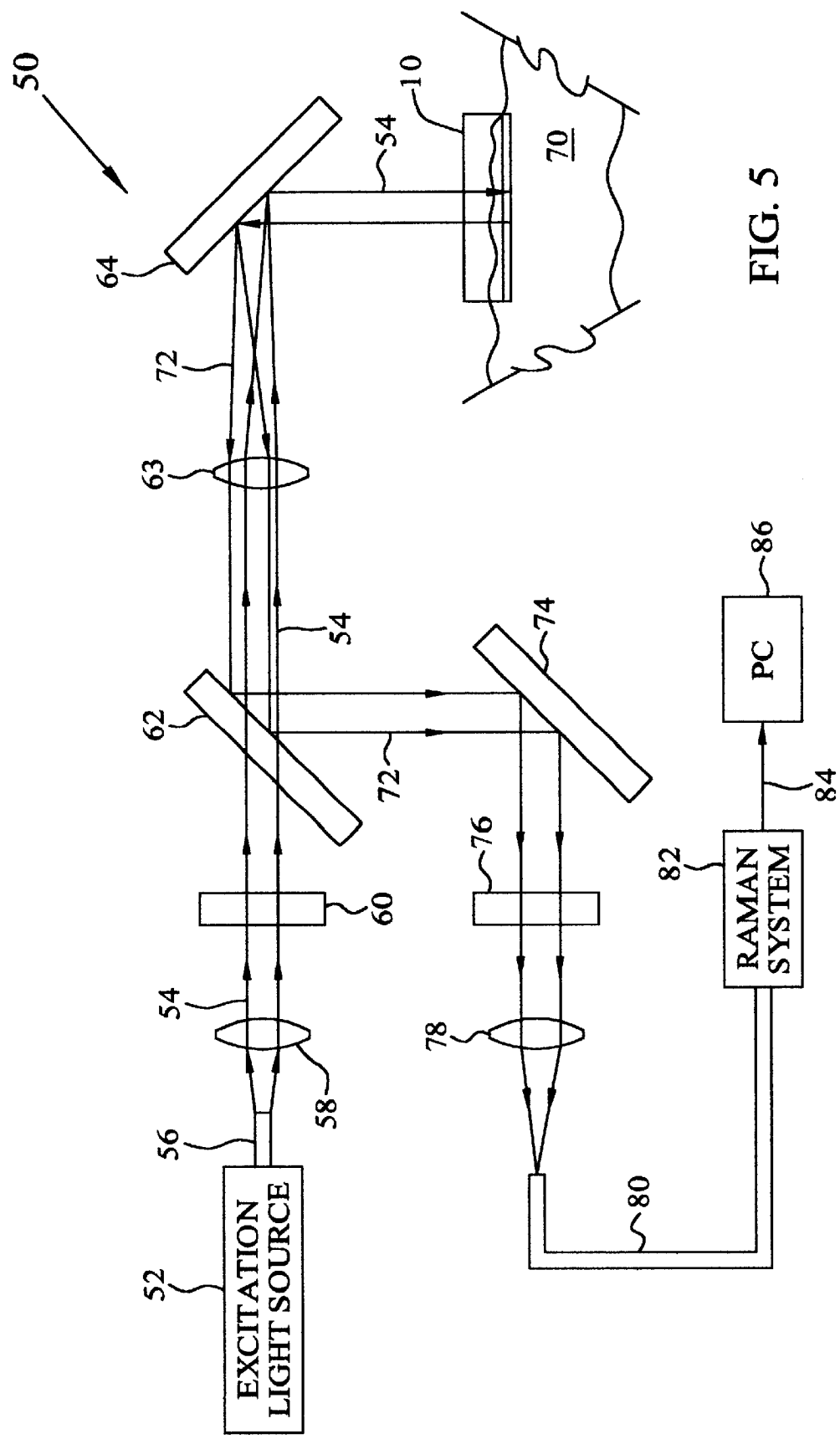
FIG. 5 shows the application of the invention in a Raman scattering system.

An example of an application of SERS substrate 10 is described with reference to FIG. 5 for obtaining Raman spectra using fiber optic system 50. Excitation light source 52, such as a Spectra Diode Laser, Inc. Model SDL-5712-H1, generates a monochromatic coherent optical signal 54 having a wavelength of 852 nm that is focused into 200 $\mu$m diameter excitation fiber 56. Optical signal 54 is emitted from excitation fiber 56 and is collimated by lens 58, such as a 6.4 mm focal length plano-convex lens manufactured by Newport, Model KPX010AR.16. Interferences due to fiber Raman emissions may be removed by band pass filter 60 (Chroma Technology Part No. 852BP) and dichroic mirror 62 (Chroma Technology Part No. 852RDM). Excitation light 54 focused by plano-convex lens 63, having a 12.7 mm focal length, onto mirror 64 reflects excitation signal 54 to SERS structure 10. SERS structure 10 may be positioned so that metal islands 16 are submerged in an aqueous environment 70. The interaction of excitation signal 54 and SERS structure 10 in the presence of an analyte of interest in aqueous environment 70 generally results in emission of Raman scattering signals 72 that are reflected by mirror 64 to lens 63. Scattering signals 72 reflected by mirror 74 are directed through long pass filter 76, such as a Chroma Technology, Part No. 852REF. Lens 78 focuses the scattered Raman emissions 72 into a 365 $\mu$m diameter collection optical fiber 80. Filter 76 blocks excitation signal 54, thereby preventing excitation of Raman emissions in collection fiber 80. Fiber 80 directs Raman emissions 72 to Raman system 82 which may be implemented as a Chromex Raman One Spectrometer. The Raman system 82 converts the Raman emissions 72 into a Raman spectrum 84. The Raman spectrum 84 from Raman system 82 is displayed and analyzed on a PC workstation 86.

Figure 6:
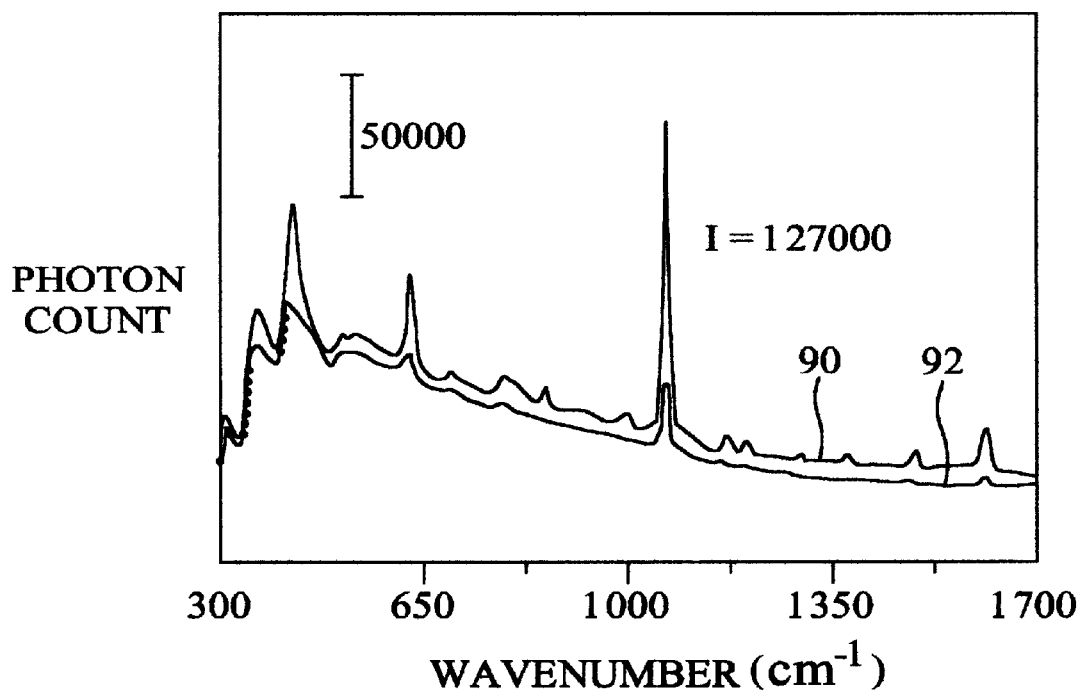
FIG. 6 shows the Raman spectra of a prior art SERS structure.
Figure 7:
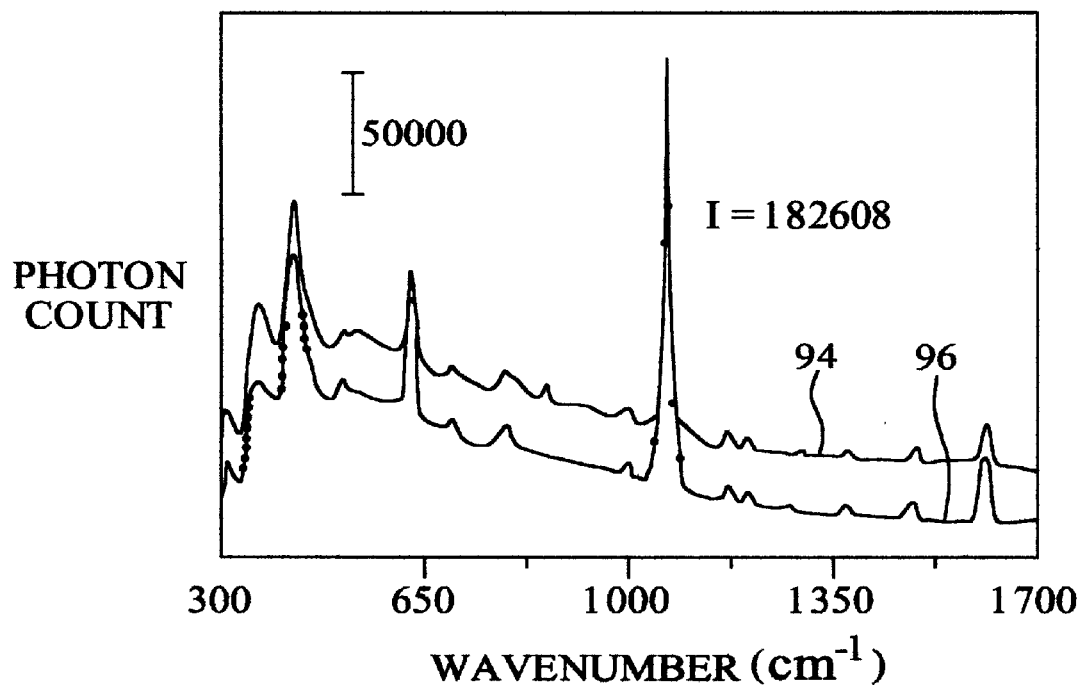
FIG. 7 shows the Raman spectra of the SERS structure shown in FIG. 1A.

FIGS. 6 and 7 show the Raman spectra of p-thiocresol chemisorbed on a thin film of gold formed on glass substrates, referenced as "SERS structures" for convenience. The horizontal axis in each of FIGS. 6 and 7 represent the wavelength of the emitted spectra. The vertical axis in each of FIGS. 6 and 7 represents optical intensity or number of photons emitted at 1073 $cm^{-1}$ detected with a Chromex Raman One Spectrometer using a diffraction grating having 600 grooves/mm and binning three horizontal pixels. The detector was operated at −50° C., and had a 100 second CCD integration time. The SERS structures were illuminated with an 852 nm DBR diode laser. Laser power at the sample was 63 mW. The structure used to generate the curves in FIG. 6 included a layer of gold having a thickness of 151 Å that was formed on a commercial white glass substrate. Curve 90 represents the number of photons generated from a SERS structure having a glass surface untreated with MCTMS. Curve 92 represents the number of photons generated from a SERS structure having a gold layer formed on a glass surface treated with MCTMS. Thus, from FIG. 6, it may be appreciated that a SERS structure comprised of a gold layer formed on commercial white glass surface that is not treated with MCTMS exhibits a good SERS response, i.e., it emits a relatively high number of photons when illuminated as described. However, the gold film has very poor adhesion to such untreated surfaces and is very fragile. Treating a commercial white glass surface with MCTMS greatly improves the durability of the bond between the gold layer and the commercial white glass surface. However, the SERS response of the MCTMS surface results in a relatively poor SERS response as revealed by curve 92 of FIG. 6.

Referring now to FIG. 7, curve 94 represents the number of photons generated from a SERS structure having gold islands formed on a transparent glass surface untreated with MCTMS and which is etched in accordance with the teachings of the present invention. Curve 96 represents the number of photons generated from SERS structure 10 having gold islands 16 that is manufactured in accordance with the teachings of the present invention. The SERS response at 1073 $cm^{-1}$ as represented by curves 94 and 96 are indistinguishable. However, the SERS structure used to generate curve 94 has very fragile gold islands which were not bonded well to the glass substrate, whereas the SERS substrate used to generate curve 96 have very durable gold islands. Thus, it may be appreciated that the present invention provides a structure having both metal islands durably bonded to a glass substrate and an excellent SERS response. Such a structure is counterintuitive because the SERS response is greatly diminished in prior art structures that employ glass substrates prepared using MCTMS.

Figure 9:
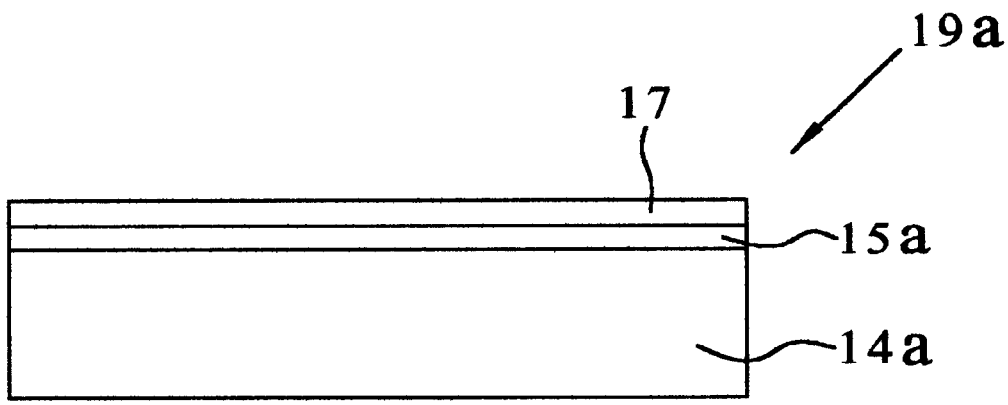
FIG. 9 is a cross-sectioned view of a multilayered SERS structure prior to the electrochemical etching.

Another embodiment of a SERS structure 1 0a that exhibits a good SERS response and is durable in an aqueous environment is manufactured using electrochemical techniques described with reference to FIGS. 9–12. Referring to FIG. 9, the fabrication of structure 19a starts by immersing substrate 14a, such as clear, borosilicate glass in a heated or boiling liquid reagent or reagents such as nitric acid, hydrofluoric acid, hydrochloric acid, or potassium hydroxide, for about 30 minutes. Such immersion removes any oils, metallic materials, and other contaminants that may be present on substrate 14a. Next, substrate 14a is removed from the boiling reagent and rinsed in either deionized or distilled water. After the water rinse, substrate 14a is immersed in hot or boiling methanol for about 30 minutes, followed by immersion in boiling acetone for about 30 minutes. This procedure removes any remaining organic contaminants. Substrate 14a then is removed from the boiling methanol and allowed to air dry, as for example, about 1 hour.

Cleaned substrate 14a then is derivitized in a silanization agent such as a 1:10 mixture by volume of (3-mercaptopropyl) trimethoxysilane (MCTMS) and ethanol for about 24 hours to form adhesion layer 15a on substrate 14a. Substrate 14a next is rinsed in ethanol to remove unreacted (3-mercaptopropyl) trimethoxysilane and allowed to air dry.

A continuous metal layer 17 made from a material such as gold, copper, or silver, is vapor deposited onto adhesion layer 15a to create a metal coated structure 19a. The metal coated structure 19a next is subjected to electrochemical techniques described with reference to FIG. 10. Metal coated structure 19a is partially immersed in an electrochemical cell 111 that includes electrolyte 101 such as a 0.1 M solution of potassium chloride (KCl) held within fluid container 101 and electrodes 105 and 108, and a working electrode 113 comprised of clamp 106 and the metallic layer 17 of metal coated structure 19a.

Metal coated structure 19a is clamped to side 102 of fluid container 104 by metallic clamp 106 so that there is electrical continuity between clamp 106 and metal layer 17. It is important that metallic clamp 106 not be immersed in the electrolyte 101 to prevent metallic ions from the clamp from contaminating the electrolyte. Also immersed in electrolyte 101 are counter electrode 105 and reference electrode 108. Counter electrode 105 preferably is made of platinum wire 107 and platinum guaze 109 that is electrically and mechanically coupled to wire 107. Electrode 105 is positioned so that guaze 109 is immersed in electrolyte 101 to increase the active surface area of electrode 105 in electrolyte 101. Reference electrode 108 preferably is made of silver/silver chloride. Electrodes 105 and 108, and clamp 106 are connected via wires 110, 112, and 114, respectively, to potentiostat 116. Potentiostat 116 maintains appropriate voltage levels at each of electrodes 105 and 108, and electrode 113 under the supervision of computer 118 via signal line 120.

Figure 12:
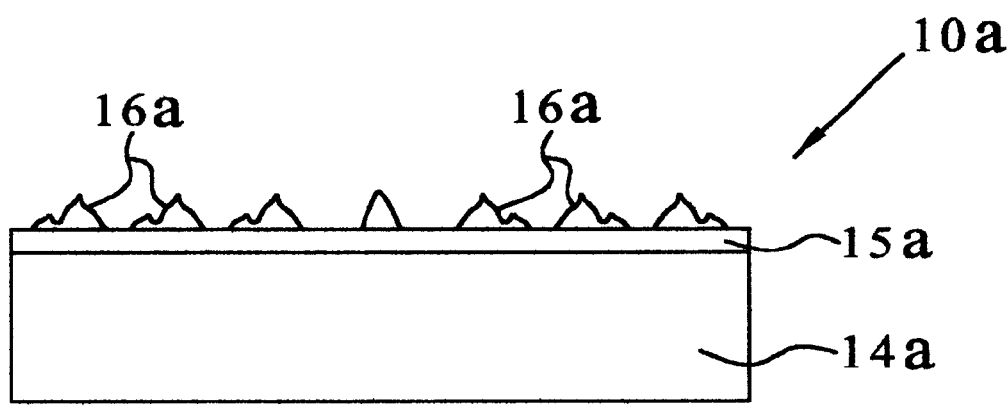
FIG. 12 is a cross-sectioned view of the multilayered SERS structure of FIG. 9 after the electrochemical etching.
Figure 10:
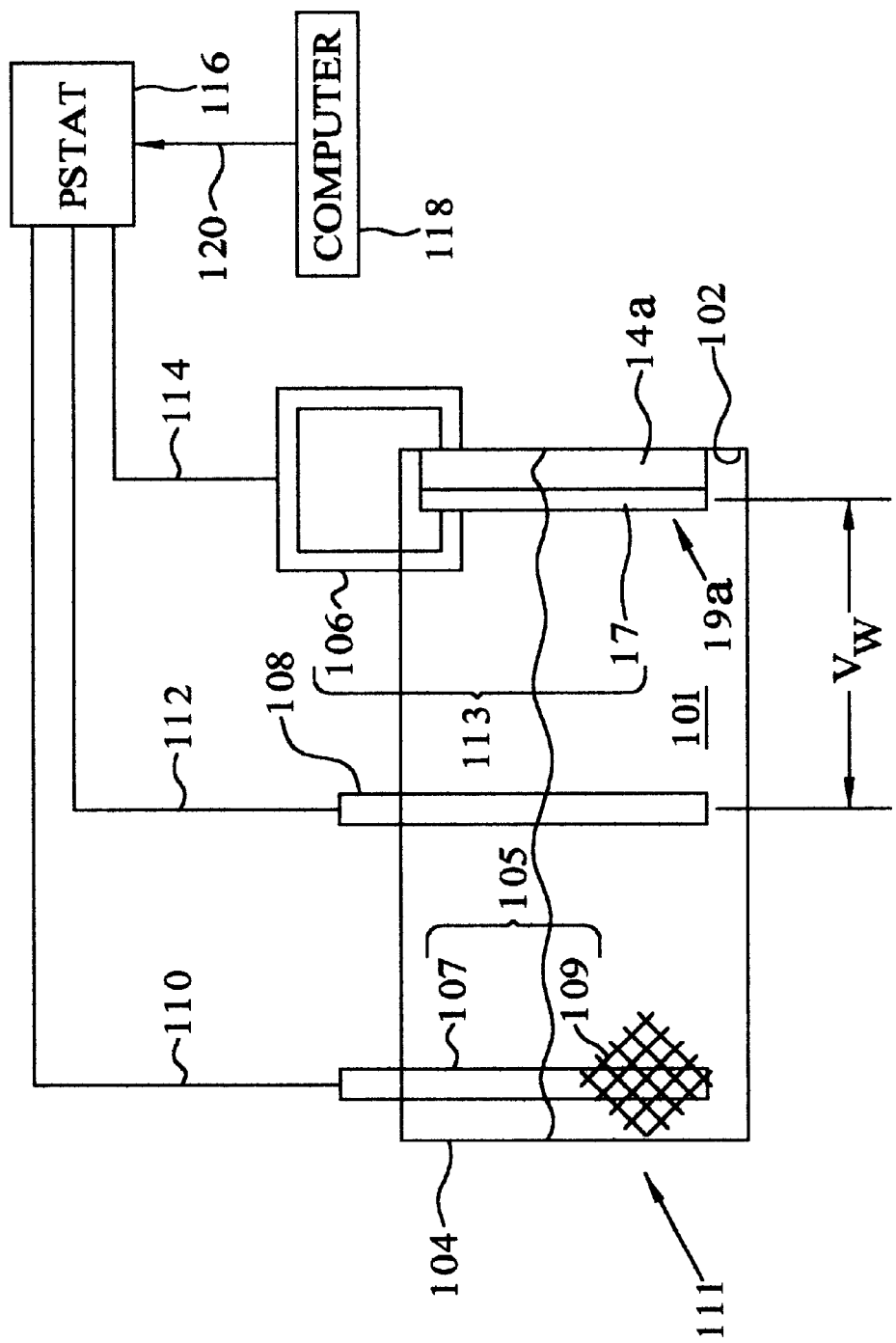
FIG. 10 shows an electrochemical cell for manufacturing the invention.
Figure 11:
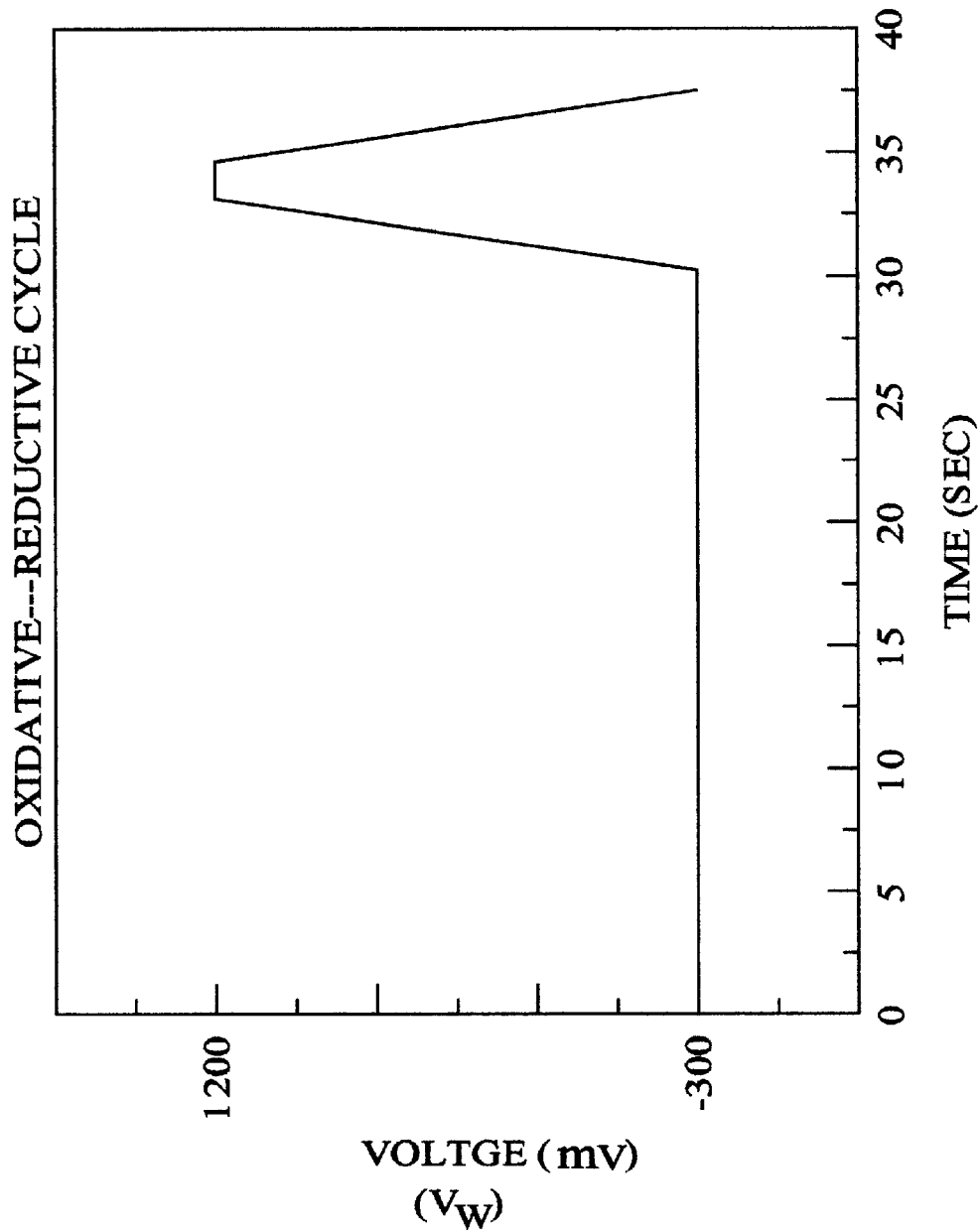
FIG. 11 is a graph representing one period of an oxidation-reduction cycle used to manufacture a SERS structure in the electrochemical cell of FIG. 10.

In the manufacture of SERS structure 10a, the voltage, $V_w$, of working electrode 113 is modulated from −300 mV to 1200 mV with respect to the voltage of reference electrode 108 for a predetermined number of oxidative-reductive cycles. An example of an oxidative-reductive cycle is shown, by way of example, in FIG. 11. Referring to FIG. 11, in an oxidative-reductive cycle, $V_w$ is held at −300 mV for about 30 seconds and then ramped to 1200 mV at a rate of about 500 mV/s. Next, $V_w$ is held at 1200 mV for about 1.3 seconds and then reduced to −300 mV at a rate of about −500 mV/s. Subjecting metal coated structure 19a to preferably 25 oxidative-reductive cycles of the type described above with reference to FIG. 11, transforms metal layer 17 into isolated metal islands 16a having an average surface roughness of about 20 Å, thereby creating a patterned metal SERS structure 10a, as shown in FIG. 12.

SERS structure 10a then may be placed in a dilute ethanolic thiol solution at ambient temperature and pressure for a period of time, such as 24 hours, so that the metal islands 16a may react with a thiol to form a durable, self-assembled monolayer 18 on the metal islands 16. Thiol coatings may be selected which have an affinity for the analyte (organic compounds, metal ions, or anions) of interest. Examples of suitable thiol coatings are identified in TABLE 1, above.

Obviously, many modifications and variations of the present invention are possible in light of the above teachings. It is therefore to be understood that within the scope of the appended claims, the invention may be practiced otherwise than as specifically described.

We claim:

1. A surface enhanced Raman scattering structure, comprising:
   a glass substrate having a roughened surface;
   an adhesion layer formed on said roughened surface;
   metal islands formed on said adhesion layer to define a metal patterned structure; and
   a self-assembled monolayer formed over said metal islands.

2. The structure of claim 1 wherein metal islands consist essentially of a metal selected from the group that includes copper, silver, and gold.

3. The structure of claim 1 wherein said metal islands are formed by vapor depositing said metal on said adhesion layer.

4. The structure of claim 1 wherein said self-assembled monolayer is a thiol selected from the group that includes 1-propanethiol, cysteamine hydrochloride, 4-(2-pyridylazo) resorcinol modified with a disulfide, and thiol derivatized dibenzo 18-crown-6.

5. The structure of claim 1 wherein said roughened surface has an average surface roughness that does not exceed about 2,500 Å.

6. The structure of claim 1 wherein said roughened surface has an average peak to peak periodicity that does not exceed about 12.5 microns.

7. The structure of claim 1 wherein said roughened surface has an average surface roughness that does not exceed about 2,500 Å and an average peak to peak periodicity that does not exceed about 12.5 micro.

* * * * *